United States Patent [19]

Ohtani et al.

[11] Patent Number: 5,585,501
[45] Date of Patent: Dec. 17, 1996

[54] METHOD FOR THE REDUCTION OF ALLYL ALCOHOLS

[75] Inventors: Mitsuaki Ohtani, Nara; Takaharu Matsuura, Settsu; Yoshinori Hamada, Kawanishi; Isamu Yamada, Neyagawa; Teruo Sakata, Osaka; Kimio Takahashi, Iwate-ken; Morio Kishi, Kyoto, all of Japan

[73] Assignee: Shionogi & Co., Ltd., Osaka, Japan

[21] Appl. No.: 453,773

[22] Filed: May 30, 1995

Related U.S. Application Data

[63] Continuation of Ser. No. 971,461, Nov. 4, 1992, abandoned.

[30] Foreign Application Priority Data

Nov. 19, 1991 [JP] Japan ...................... 3-331348

[51] Int. Cl.$^6$ .................................. C07D 307/83
[52] U.S. Cl. .......................... 549/305; 549/312
[58] Field of Search ...................... 549/305, 312

[56] References Cited

PUBLICATIONS

Doyle et al., J. Org. Chem. vol. 41, No. 8, pp. 1393–1396 (1976).
Adlington et al., Tetrahedron Letters, No. 34, pp. 2955–2958 (1976).
Brewster et al., J. Org. Chem. vol. 29, pp. 116–121 (Jan. 1964).
Corey et al., J. Amer. Chem. Soc., vol. 93, No. 6, pp. 1491–1493 (1971).

*Primary Examiner*—Ba K. Trinh
*Attorney, Agent, or Firm*—Wenderoth, Lind & Ponack

[57] ABSTRACT

A method for reduction of an allyl alcohol-type compound, specific to its allylic hydroxyl group, being carried out without any side reactions such as reduction of other portions of the compound or allylic rearrangement, which comprises treating the compound with trialkylsilane in the presence of $AlX_3$, wherein X refers to a halogen atom.

1 Claim, No Drawings

METHOD FOR THE REDUCTION OF ALLYL ALCOHOLS

This application is a continuation of now abandoned Ser. No. 07/971,461 filed Nov. 4, 1992.

FIELD OF THE INVENTION

This invention relates to a method for reducing allyl alcohols, more specifically, it relates to a method for a specific reduction of allylic hydroxyl group applicable to a wide variety of allyl alcohol-type compounds.

There are many allyl alcohol-type compounds (hereinafter, those having allyl alcohol-portion are simply referred to as allyl alcohols) useful for the production of clinically important compounds. For example, a derivative of prostaglandin, 15-deoxyprostaglandin, which has recently been reported to be effective for the treatment of glaucoma can be produced from a precursor through the reduction of the 15-hydroxyl group at an allyl alcohol-portion. The method of the present invention is particularly useful for the specific reduction of said 15-hydroxyl group to produce the desired 15-deoxyprostaglandins efficiently.

BACKGROUND OF THE INVENTION

A typical indirect reduction of a hydroxyl group of compounds having a partial structure of allyl alcohol has been reported in *Proc. Natl. Acad. Sci. USA* 74, 4007, (1977), where the hydroxyl group is brominated before the reduction by $NaBH_4$.

A direct reduction using $NaBH_3CN/ZnI_2$ has been reported in *J. Org. Chem.* 51, 3038 (1986). This method, however, lacks selectivity and involves the reduction of groups other than the desired allylic hydroxyl group and tends to induce allyllic rearrangement, which leads to a poor yield of the product.

Another method which comprises the use of $LiAlH_4/AlCl_3$ has been reported in *Tetrahedron Letters*, 2447 (1976). It is generally known that the method accompanied by reduction of ester groups.

Thus, the existing methods are not suited for the selective reduction of allyl alcohols because they involve side reactions such as the allylic rearrangement and the reduction of undesirable substituents such as ester groups, which are mainly caused by insufficient selectivity. Accordingly, it was difficult to reduce specifically an allylic hydroxyl group of an allyl alcohol-portion to give a desired product in high yield. In addition, an isomer produced by the allylic rearrangement is hardly separable from the desired unsaturated compound even by a chromatographic process, which also lowers the yield.

Accordingly, it has been demanded to establish a method capable of reducing specifically a hydroxyl group of allylic alcohol, avoiding undesirable allyl rearrangement, for an industrial production of the desired product.

SUMMARY OF THE INVENTION

In view of the above, the present inventors made an extensive study and found that an allylic hydroxyl group of allyl alcohols can be specifically reduced when said compound is treated with trialkylsilane in the presence of $AlX_3$, wherein X refers to a halogen atom.

DETAILED DESCRIPTION OF THE INVENTION

Thus, the present invention provides a method for reduction of an allyl alcohol-type compound, specific to its allylic hydroxyl group, which comprises treating said compound with trialkylsilane in the presence of $AlX_3$, wherein X refers to a halogen atom.

For purposes of the present invention, as disclosed and claimed herein, "an allyl alcohol-type compound" or simply "an allyl alcohol" means a compound of formula II:

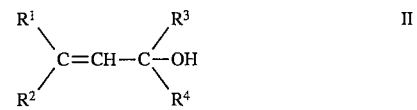

wherein $R^1$, $R^2$, $R^3$, and $R^4$, each is independently substituent. The compound of formula II is also referred to as compound II.

The substituent is not critical for the present invention, and can be selected from, for example, a group consisting of hydrogen, lower alkyl, cycloalkyl, cycloalkyl-lower alkyl, lower alkoxy, amino, mono(lower alkyl)amino, di(lower alkyl)amino, carboxyl, aryl, heterocyclic, aralkyl, aryloxy, aralkyloxy, alkanoyloxy, aroyloxy, alkylthio, alkoxycarbonyl, aryloxycarbonyl, aralkyloxycarbonyl, hydroxycarbamoyl, carbazoyl, carbamoyloxy, and the like. It is preferable that at least one of $R^1$ and $R^2$ is a group capable of affording greater steric hindrance than any of $R^3$ and $R^4$. In this regard, it is preferred that $R^1$ and $R^2$, each is independently selected from the group consisting of dialkyl methyl group such as i-propyl, i-butyl, s-butyl, t-butyl, i-pentyl, neopentyl, s-pentyl, t-pentyl, neohexyl, i-hexyl, s-hexyl, t-hexyl, and the like; cycloalkyl; aryl; heterocycle; and the like. On the contrary, both $R^3$ and $R^4$ are preferably a group which gives steric hindrance as little as possible, and more preferably, at least one of them is hydrogen. The above-mentioned substituents may have one or more substituents selected from hydroxy, amino, carboxyl and the like.

Examples of compounds of formula (II) which can be successfully reduced by the present method include a compound of the following formula I, which compound will be hereinafter referred to as compound I.

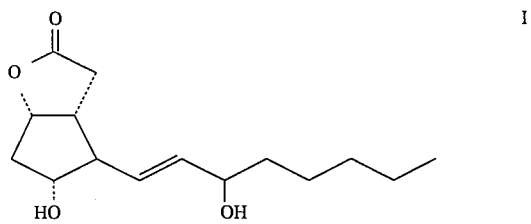

The compound I, when reduced at the 15-hydroxyl group, wherein said position is numbered according to the accepted numbering method for prostaglandins, yields a compound of the following formula III which can be used as an intermediate for the production of 15-deoxyprostaglandin, said compound being useful in the treatment of glaucoma.

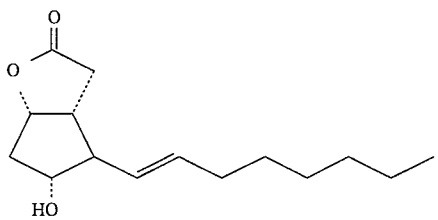

III

A hydroxy-protected derivative of compound III has been disclosed in Japanese Patent Application No. 57476/1990.

According to the method of the invention, the specific reduction of an allyl alcohol is effected by the treatment of said alcohol with trialkylsilane in the presence of $AlX_3$, wherein X is a halogen atom. When the method of the present invention is put into practice, an allyl alcohol is conveniently used as it is. Alternatively, it may be halogenated before the reduction.

As will be easily appreciated from the above, one of the most outstanding features of the invention resides in that it provides a direct reduction of an allyl alcohol to give a desired product in high yield. The direct reduction is highly desirable in terms of the saving of reagents, time, labors and the like. However, the two-step process where an allyl alcohol is halogenated before the reduction of the present invention also gives the desired product in high yield, and such a two-step process is also included within the scope of the invention.

The halogenation can be chlorination, bromination or iodination, each being performed by a known method per se. For instance, the bromination can be carried out using an organophosphorus compound such as triphenylphosphine and a brominating agent such as carbon tetrabromide.

The term "$AlX_3$" refers to an aluminium halide such as $AlF_3$, $AlCl_3$, $AlBr_3$ or $AlI_3$, preferably, $AlCl_3$.

In general, about one or more moles of $AlX_3$ is used per one mole of compound II, and preferably about three or more moles of $AlX_3$ is used per one mole of compound I.

The term "trialkylsilane" refers to a compound formed by substituting a Si atom by three alkyl groups. Examples of trialkylsilane include trimethylsilane, triethylsilane, tripropylsilane, dimethylethylsilane, diethylmethylsilane, and the like.

Generally, about one or more moles of trialkylsilane is used per one mole of compound II, and preferably more than five moles of trialkylsilane is used per one mole of compound I.

The reduction of the present invention can be accomplished in an appropriate solvent at a suitable temperature for a period sufficient for the production of the desired compound.

An appropriate solvent can be selected from those suited for a given compound to be reduced. Typically, halogenated hydrocarbons such as dichloromethane, chloroform and the like can be used. Solvents commonly used for the Friedel-Crafts reaction, for example, benzene, nitrobenzene, carbon disulfide and the like are also available.

The reaction temperature may also vary depending on various factors such as the kind of compound II and the amount of reagents, and is not necessarily limited to a given temperature. The reaction is generally carried out at a temperature of from about −25° C. to about 50° C., preferably from about −10° C. to about 40° C. Under the conditions, the reaction may be completed within about several minutes to about several hours.

When the compound II contains any other substituents susceptible to the reduction of the invention, such as additional hydroxyl group, amino group, or carboxyl group, such substituents may be preferably protected before the reduction using any of known protecting groups per se.

For instance, hydroxy-protecting groups can be selected from those currently used in the art as long as they are not deprotected under the reaction conditions of the reduction according to the present invention. Such protecting groups can be found in the literature (*Protective Groups in Organic Synthesis*, T. W. Greene, John Wiley & Sons, Inc., New York, pp. 10, 1981). Among those described therein, there are preferable types of groups, for example, alkyl(thio)ether type, for example, methyl, methoxyethyl, methylthiomethyl, 2-methoxyethoxymethyl, 1-ethoxyethyl or the like; silylether type, for example, triethylsilyl, t-butyldimethylsilyl, t-butyldiphenylsilyl, or the like; acyl type, for example, acetyl, benzoyl, p-methylbenzoyl, o-methoxybenzoyl, p-phenylbenzoyl, or the like; aralkyl type, for example, benzyl, p-methoxybenzyl or the like. For the reduction of compound I, p-phenylbenzoyl is preferable in terms of the facilitation of crystallization.

For purposes of the present invention, as disclosed and claimed herein, the following terms are defined as below.

The term "lower alkyl" refers to a straight or branched $C_1$—$C_6$ alkyl group. Examples of such groups include methyl, ethyl, n-propyl, i-propyl, n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl and the like, and each group may have one or more substituents selected from hydroxyl, amino, or carboxyl group.

The term "cycloalkyl" refers to $C_3$—$C_7$ cycloalkyl group. Example of such groups include cyclopropyl, cyclobutyl, cyclopentyl, cyclohexyl and cycloheptyl, and each group may have one or more substituents such as hydroxyl or acetoxy group, and may be condensed with a lactone ring.

The term "cycloalkyl-lower alkyl" refers to a group formed by substituting lower alkyl defined above by cycloalkyl defined above. Examples of such groups include cyclopropyl methyl, cyclobutyl ethyl, cyclohexyl n-propyl and the like.

The term "lower alkoxy" refers to straight or branched $C_1$—$C_6$ alkoxy group. Example of such groups include methoxy, ethoxy, n-propoxy, i-propoxy, n-butoxy, i-butoxy, s-butoxy, t-butoxy, n-pentoxy, i-pentyloxy, neopentyloxy, s-pentyloxy, t-pentyloxy, n-hexyloxy, neohexyloxy, i-hexyloxy, s-hexyloxy, t-hexyloxy and the like, each of which may have one or more substituents selected from hydroxyl, amino, or carboxyl group.

The term "mono-lower alkylamino" refers to a group formed by substituting an amino group by a lower alkyl group selected from those defined above. Examples of such groups include methylamino, ethylamino, n-propylamino, i-propylamino, n-butylamino, i-butylamino, s-butylamino, t-butylamino, n-pentylamino, i-pentylamino, n-hexylamino, i-hexylamino and the like.

The term "di-lower alkylamino" refers to a group formed by substituting an amino group by two lower alkyl groups selected from those defined above. Examples of such groups include dimethylamino, diethylamino, N-methylethylamino, N-methyl-propylamino, N-ethyl-propylamino, dipropylamino, dibutylamino, dipentylamino, dihexylamino, N-pentyl-hexylamino and the like. The two substituents, together with the nitrogen atom to which they are attached, may form a cyclic-imino group which contains additional nitrogen, oxygen and/or sulfur atom. Examples of such cyclic-imino groups include polymethylene imino (e.g., pyrrolidino, piperidino, piperazino), N-substituted piperadizo, morpholino, thiomorpholino, homopiperazino, N-substituted homopiperazino and the like.

The term "aryl" refers to aryl radicals including phenyl, (α- or β-) naphthyl, and the like. These groups may have one or more substituents selected from hydroxyl, amino, carboxyl or the like.

The term "heterocyclic group" refers to aromatic or completely saturated heterocyclic group.

The term "aromatic heterocyclic group" refers to an aromatic ring containing one or more heteroatoms selected from nitrogen, oxygen and sulfur which may be condensed with other aromatic rings. Examples of such groups include pyrrolyl, indolyl, carbazolyl, imidazolyl, pyrazolyl, benzimidazolyl, indazolyl, indolizinyl, pyridyl, quinolyl, isoquinolyl, acridinyl, phenanthridinyl, pyridazinyl, pyrimidyl, pyrazinyl, cinnolinyl, phthalazinyl, quinazolinyl, naphthyridinyl, quinoxalinyl, phenazyl, 1,3,5-triazinyl, 1,2,4-triazinyl, 1,2,3-triazinyl, purinyl, puteridinyl, isoxazolyl, benzisoxazolyl, 1,2,3-oxadiazolyl, 1,2,4-oxadiazolyl, 1,2,5-oxadiazolyl, 1,3,4-oxadiazolyl, benzoxadiazolyl, isothiazolyl, benzisothiazolyl, thiazolyl, benzthiazolyl, 1,2,3-thiadiazolyl, 1,2,4-thiadiazolyl, 1,2,5-thiadiazolyl, 1,3,4-thiadiazolyl, benzthiadiazolyl, furanyl, benzofuranyl, thienyl, benzothienyl and the like. Each group may have one or more substituents selected from hydroxyl, amino, carboxyl or the like.

The term "completely saturated heterocyclic group" refers to 3- or 8-membered completely saturated heterocyclic ring containing one or more heteroatoms selected from nitrogen, oxygen and sulfur. Examples of such groups include azetidinyl, pyrrolidinyl, piperidinyl, morpholinyl, thiomorpholinyl, piperazinyl, oxiranyl, thietanyl and the like. Each group may have one or more substituents selected from hydroxyl, amino, carboxyl or the like.

The term "aralkyl" refers to a group formed by substituting a lower alkyl group as defined above by an aryl group as defined above. Examples of such groups include benzyl, phenethyl, phenylpropyl, (α- or β-) naphthylmethyl and the like.

Examples of "aryloxy" include phenyloxy, (α- or β-) naphthyloxy and the like. Each group may have one or more substituents selected from hydroxyl, amino, carboxyl or the like.

Examples of "aralkyloxy" include phenethyloxy, phenylpropyloxy and the like.

The term "alkanoyloxy" refers to a group formed by substituting a carbonyloxy group by a lower alkyl group as defined above. Examples of such groups include acetyl, propionyl, butyloyl and the like.

Examples of "aroyloxy" include benzoyloxy, naphthoyloxy and the like. Each group may have one or more substituents selected from hydroxyl, amino, carboxyl or the like.

The term "alkylthio" refers to a group formed by binding a lower alkyl group as defined above to a sulfur atom. Examples of such groups include methylthio, ethylthio, propylthio, butylthio, hexylthio and the like.

The term "alkoxycarbonyl" refers to a group formed by substituting a carbonyl group by a lower alkyl as defined above. Examples of such groups include methoxycarbonyl, ethoxycarbonyl, propoxycarbonyl and the like.

Examples of "aryloxycarbonyl" include phenyloxycarbonyl, (α- or β-) naphthyloxycarbonyl and the like. Each group may have one or more substituents selected from hydroxyl, amino, carboxyl or the like.

Examples of "aralkyloxycarbonyl" include phenethyloxycarbonyl, phenylpropyloxycarbonyl and the like.

The following example are set forth to describe the invention in detail but is in no way meant to be construed as limiting the scope thereof.

REFERENCE EXAMPLE 1

Preparation of (1S, 6R, 7R)-2-Oxa-3-oxo-6-[(3R)-bromo-(1E)-octenyl]-7-p-phenylbenzoyloxy-cis-bicyclo[3.3.0]octane (compound 2) and (1S, 6R, 7R)-2-Oxa-3-oxo-6-[1-bromo-(3E)-octenyl]-7-p-phenylbenzoyloxy-cis-bicyclo[3.3.0]octane (compound 3)

To a solution of (1S, 6R, 7R)-2-oxa-3-oxo-6-[(3S)-hydroxy-(1E)-octenyl]-7-p-phenylbenzoyloxy-cis-bicyclo [3.3.0]octane (compound 1) (750 mg, 1.67 mmole) in dichloromethane (15 ml) are added carbon tetrabromide (665 mg, 2.00 mmole) and triphenylphosphine (1.053 g, 4.00 mole) at 0° C. and the mixture is stirred for 30 min at the same temperature. The reaction mixture is subjected to a column chromatography (silica gel, 25 g) using ethyl acetate/hexane (1:3) as eluent to obtain a crude product (700 mg). When the crude product is chromatographed on Lobar column (eluent: ethyl acetate/hexane; 1:3), the title compounds 3 (96 mg, 11%) and 2 (501 mg, 59%) are eluted in this order.

The starting material, compound 1, is described in the *Journal of the American Chemical Society*, 93(6), pp. 1491 (1971). Thus, successive alkylation of cyclopentadiene with chloromethyl benzyl ether using the thallium method, cupric fluoroborate catalyzed addition of 2-chloroacrylonitrile, and hydrolysis using potassium hydroxide in dimethyl sulfoxide afforded the bicylic ketone I. Crude I was subjected to reaction with m-chloroperbenzoic acid-sodium bicarbonate in methylene chloride at 0° to −10° to form a lactone which was directly converted into the hydroxy acid II by base-catalyzed hydrolysis. The acid II was isolated and purified as the crystalline (racemic) ammonium salt (formed by addition of anhydrous ammonia to a solution of II in ether at 0°), mp 134°–135° (40–50% yield overall from thallous cyclopentadienide). The hydroxy acid II was resolved (60–70% yield) by recrystallization of the (+)-amphetamine salt; found for the resolved salt, mp 112.5°–113.5°, $[\alpha]^{25}D+17°$ (c 1.5, methanol).

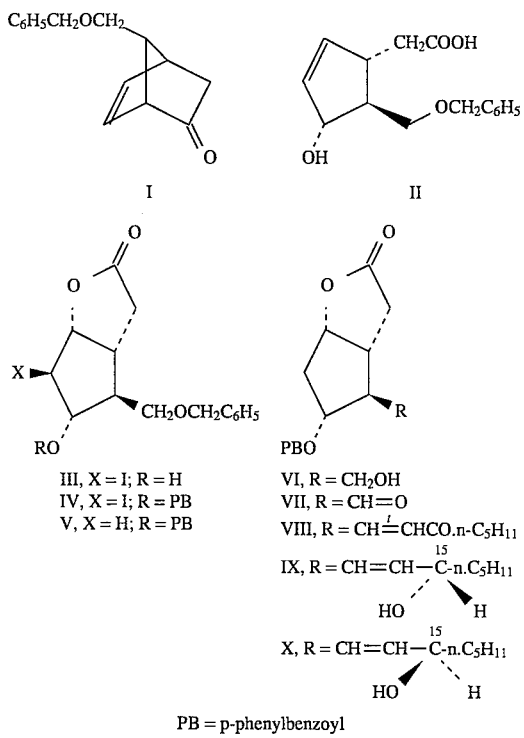

PB = p-phenylbenzoyl

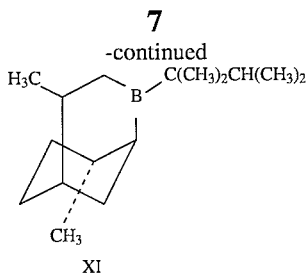

XI

Iodolactonization of II afforded III, mp 120°–122° (from methylene chloride-hexane), $[\alpha]^{25}D$–34.0° (c 1.1, $CHCl_3$) (>97% yield), which was esterified with p-phenylbenzoyl chloride (PBCl) in pyridine at 25° for 1 hr to form the ester lactone IV, mp 171.5°–172° (from methylene chloride-hexane), $[\alpha]^{25}D$+0.80° (c 1.21, $CHCl_3$) (97% yield), deiodination of which was accomplished using tributyltin hydride in benzene at 55° to give V, mp 97°–98° (from methylene chloride-isopropyl ether), $[\alpha]^{25}D$-85.0° (c 1.0, $CHCll_3$) (>98% yield). Debenzylation of V was accomplished by treatment with hydrogen at 45 psi at 25° for 4 hr in 2:1 ethyl acetate-ethanol containing a small amount of hydrochloric acid (ca. 0.01 N) using 5% palladium/charcoal catalyst to form the alcohol VI, mp 130°–131° (from methylene chloride-hexane), $[\alpha]^{25}D$-87.3° (c 1.0, $CHCl_3$) (97% yield). Collins oxidation of VI gave the crystalline aldehyde VII which, when treated (without purification) with the sodium salt of dimethyl 2-oxoheptylphosphonate in dimethoxyethane, yielded the crystalline enone VIII, mp 81°–82.5° (from isopropyl alcohol-hexane), $[\alpha]^{25}D$-146° (c 0.20, $CHCl_3$) (80% yield from VI).

In previous work the reduction of the ketonic function in enone intermediates such as VIII was effected using zinc borohydride as reagent, which yielded a 1:1 mixture of epimeric 15α and 15β alcohols. Other standard hydride-type reducing agents were found to be less satisfactory (or at best equivalent), since the ratio of 15α and 15β alcohols (prostaglandin numbering used) was never greater than 1:1 and since troublesome by-products, most important of which is the ketone resulting from saturation of the α, β double bond, were usually formed. For example, the reaction of 1 equiv of diisobutylaluminum hydride with VIII in toluene at –80° yielded a complex mixture containing the corresponding saturated ketone and a relatively small amount of the alcohols IX and X in equal proportion. The optically active reagent diisopinocamphenylborane, which has been found to reduce saturated ketones of type $RCOCH_3$ to secondary alcohols ($RCHOHCH_3$) of 11–30% optical purity, reacts with VIII in tetrahydrofuran solution (–45°) chiefly (~90%) with reduction of the α,β carboncarbon double bond. The optically active borohydride ions prepared by the reaction of diisopinocamphenylborane with methylor tert-butyllithium were much more promising, however. These were found to afford 1,2- and 1,4-reduction products in a ratio of 1.5–2.5:1 in tetrahydrofuran at –78°, and it was further observed that the addition of certain Lewis bases dramatically attenuated the 1,4-reduction pathway. The most effective base studied thus far is hexamethylphosphoramide (HPA). Utilizing 4 equiv of a reagent prepared from optically active diisopinocamphenylborane and methyllithium (1:1) to which was added 10 equiv of HPA with tetrahydrofuran-ether as solvent under nitrogen at –97 to –100° (pentane-liquid nitrogen bath), the ketone VIII was converted in 5 hr to a product consisting of only 2.8% of the α, β reduction product, 66% of the desired 15α alcohol IX, and 31% of the 15β alcohol X. The corresponding reaction with the reagent diisopinocamphenyl-tert-butylborohydride afforded slightly better results: 1% of the α, β reduction product, 68% of the desired IX, and 31% X. The alcohols IX and X can be isolated in pure condition by chromatography on silica gel using ether as solvent. The 15α derivative IX, which was obtained as an oil, was readily converted to prostaglandins $F_{2\alpha}$ and $E_2$ (natural form) by the route previously described. The 15β derivative X was obtained as a crystalline solid, mp 77°–78.5°, $[\alpha]^{25}D$–116° (c 0.44, $CHCl_3$). Both IX and X underwent oxidation by manganese dioxide to afford the enone VIII (>97% yield).

REFERENCE EXAMPLE 2

Preparation of (1S, 6R, 7R)-2-Oxa-3-oxo-6-[(1E)-octenyl]-7-p-phenylbenzoyloxy-cis-bicyclo[3.3.0]octane (compound 4)

To a solution of compound 2 (451 mg, 0.882 mmole) prepared in the Reference Example 1 in dimethyl sulfoxide (9 ml) is added sodium borohydride (67 mg, 1.765 mmole) at room temperature and the mixture stirred for 2 hr. After the addition of dilute hydrochloric acid, the mixture is extracted with dichloromethane. The extract is washed with water, dried, and distilled to remove the solvent to yield a colorless oil (520 mg). The oil is then loaded onto a silica gel (2.6 g) column. When the column is eluted with ethyl acetate/hexane (1:3) and ethyl acetate, successively, a colorless oil (330 mg) and yellowish oil (68 mg) are obtained, respectively. The purification of the colorless oil by Lobar column (eluent: ethyl acetate/hexane; 1:3) gives the title compound 4 (214 mg, 56%).

REFERENCE EXAMPLE 3

Preparation of (1S, 6R, 7R)-2-Oxa-3-oxo-6-[(2E)-octenyl]-7-p-phenylbenzoyloxy-cis-bicyclo[3.3.0]octane (compound 5)

To a solution of compound 3 (129 mg, 0.235 mmole) prepared in the Reference Example 1 in dimethyl sulfoxide (2 ml) is added sodium borohydride (18 mg, 0.47 mmole) at room temperature. Thereafter, the mixture is treated in the same manner as that described in the Reference Example 2 to obtain a colorless oil (120 mg). The oil is loaded onto a silica gel (1.2 g) column and eluted with ethyl acetate/hexane (1:3) to obtain an oil (72 mg). The purification of the oil by Lobar column (eluent: ethyl acetate/hexane; 1:3) gives the title compound 5 (33 mg, 33%).

EXAMPLE 1

Direct Reduction of Compound 1

To a solution of triethylsilane (106.8 ml, 0.669 mole) in dichloromethane (360 ml) are added with successively aluminium chloride (71.4 g, 0.5352 mole) and a solution of (1S, 6R, 7R)-2-oxa-3-oxo-6-[(3S)-hydroxy-(1E)-octenyl]-7-p-phenylbenzoyloxy-cis-bicyclo[3.3.0]octane (compound 1) (60 g, 0.1338 mole) in dichloromethane (180 ml) at 0° C., and the mixture stirred for 1 hr at the same temperature. The reaction mixture is poured into a chilled dilute hydrochloric acid, followed by extraction with dichloromethane. The extract is washed with water, dried, and distilled to remove the solvent. The residue (84 g) is loaded onto a silica gel (170 g) column and eluted with hexane-dichloromethane-ethyl acetate (from 40:10:3 to 40:10:5) to yield a mixture of compounds 4 and 5 (64 g, compound 4:compound 5=97:3 on HPLC). The product, when recrystallized from ethyl acetate/hexane, gives compound 4 (55.3 g, 96%). M.p.=74°–76° C.

EXAMPLE 2

Direct Reduction of Compound 1'

To a solution of triethylsilane (11 ml, 0.069 mole) in dichloromethane (37 ml) are added successively aluminium chloride (7.36 g, 0.052 mole), and a solution of (1S, 6R, 7R)-2-oxa-3-oxo-6-[(3R)-hydroxy-(1E)-octenyl]-7-p-phenylbenzoyloxy-cis-bicyclo[3.3.0]octane (compound 1') (6.19 g, 0.0138 mole) in dichloromethane (18 ml) at 0° C., and the mixture stirred for 1 hr at the same temperature. Thereafter, the resultant reaction mixture is treated in the same manner as described in Example 1 to yield a mixture of compounds 4 and 5 (6.5 g, compound 4:compound 5=96:4 on HPLC). The product, when recrystallized from ethyl acetate/hexane, gives compound 4 (5.53 g, 93%). M.p.=74°–76° C.

The compound 1' is also described in the same literature as that shown in Example 1 above.

EXAMPLE 3

Direct Reduction of a Mixture of an Equal Amount of Compounds 1 and 1'

To a solution of triethylsilane (53.4 ml, 0.3345 mole) in dichloromethane (180 ml) are added successively aluminium chloride (35.67 g, 0.2676 mole) and a solution of a mixture of an equal amount of compounds 1 and 1' (30 g, 0.0669 mole each) in dichloromethane (90 ml) at 0° C., and the mixture stirred for 1 hr at the same temperature. Thereafter, the reaction mixture is treated in the same manner as described in Example 1 to yield a mixture of compounds 4 and 5 (38 g, compound 4:compound 5=97:3 on HPLC). The product, when recrystallized from ethyl acetate/hexane, gives compound 4 (27.33 g, 95%). M.p.=74°–76° C.

EXAMPLE 4

Reduction of Compound 1 via the Bromination

To a solution of compound 1 (61.92 g, 0.138 mole) in dichloromethane (750 ml) are added successively triphenylphosphine (76.04 g, 0.290 mole) and carbon tetrabromide (48.9 g, 0.145 mole) in dichloromethane (75 ml) at −40° C. and the mixture stirred for 1 hr. The reaction mixture is then concentrated to about half of the volume, and triethylsilane (110 ml, 0.689 mole) and aluminium chloride (73.64 g, 0.552 mole) are added thereto at room temperature After stirring for 1 hr at 35°–40° C. the resultant reaction mixture is poured into a chilled dilute hydrochloric acid, which is followed by extraction with ethyl acetate. The extract is then washed with water, dried, and distilled to remove the solvent. To the residue is added toluene-hexane (4:1) and the precipitates are removed by filtration. Purification of the filtrate by a silica gel (600 g) column using ethyl acetate/hexane as eluent gives a mixture of compounds 4 and 5 (44.94 g, 75.3%, compound 4:compound 5=9:1). The product, when recrystallized from ethyl acetate/hexane, yields compound 4 (25 g, 42%).

EXAMPLE 5

Reduction of Compound 1' via the Bromination

To a solution of compound 1' (45 mg, 0.1 mmole) in dichloromethane (5 ml) are added successively triphenylphosphine (55 mg, 0.21 mmole) and carbon tetrabromide (34.8 g, 0.105 mmole) at −20 ° C., and the mixture stirred for 30 min at room temperature. After the addition of triethylsilane (80 µl, 0.5 mmole) and aluminium chloride (53.3 mg, 0.4 mmole), the mixture is stirred for 1 hr at room temperature. The reaction mixture is poured into ice-cold water and extracted with dichloromethane. The extract is then washed with water, dried, and distilled to remove the solvent. Purification of the residue by silica gel (5 g) column using ethyl acetate/hexane as eluent gives a mixture of compounds 4 and 5 (33 mg, 76%, compound 4:compound 5=91:9 on HPLC).

EXAMPLE 6

Reduction of a Mixture of an Equal Amount of Compounds 1 and 1' via the Bromination To a solution of a mixture of an equal amount of compounds 1 and 1' (45 mg, 0.1 mmole each) in dichloromethane (5 ml) are added successively triphenylphosphine (55 mg, 0.21 mmole) and carbon tetrabromide (34.8 mg, 0.105 mmole) at −20° C., and the mixture stirred for 30 min at room temperature. After the addition of triethylsilane (80 µl, 0.5 mmole) and aluminium chloride (53.3 mg, 0.4 mmole), the mixture is stirred for 1 hr at room temperature. Thereafter, the reaction mixture is treated in the same manner as that described in Example 5 to obtain a mixture of compounds 4 and 5 (33 mg, 76%, compound 4:compound 5=96:4 on HPLC).

As can be seen from the previous Examples, the present invention provides a method for reduction of an allyl alcohol-type compound, specific to its allylic hydroxyl group without any effects on other portions of the compound such as ester group and avoiding the allylic rearrangement, thereby giving the objective unsaturated compounds in high yield.

What we claim is:

1. A method for reducing an allyl alcohol-type compound represented by the formula (I):

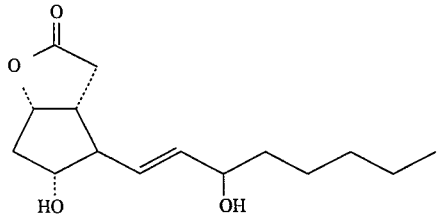

wherein the hydroxyl group attached to the ring is optionally protected by a hydroxyl protecting group, to produce a corresponding unsaturated compound of the formula (III):

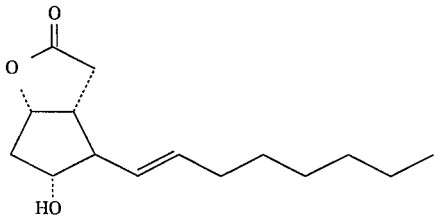

which comprises treating said compound (I) with trialkylsilane in the presence of $AlX_3$, wherein X is a halogen atom.

* * * * *